US012582627B2

(12) United States Patent
Cuenoud et al.

(10) Patent No.: US 12,582,627 B2
(45) Date of Patent: Mar. 24, 2026

(54) MCT FORMULATIONS FOR IMPROVING COGNITIVE FUNCTIONS

(71) Applicants: SOCIETE DES PRODUITS NESTLE S.A., Vevey (CH); SOCPRA SCIENCES SANTE ET HUMAINES, S.E.C., Sherbrooke (CA)

(72) Inventors: Bernard Cuenoud, Cully (CH); Stephen Cosgrave Cunnane, Sutton (CA)

(73) Assignees: SOCIETE DES PRODUITS NESTLE S.A., Vevey (CH); SOCPRA SCIENCES SANTE ET HUMAINES, S.E.C., Sherbrooke (CA)

( * ) Notice: Subject to any disclaimer, the term of this patent is extended or adjusted under 35 U.S.C. 154(b) by 634 days.

(21) Appl. No.: 17/998,891

(22) PCT Filed: May 17, 2021

(86) PCT No.: PCT/EP2021/062908
§ 371 (c)(1),
(2) Date: Nov. 15, 2022

(87) PCT Pub. No.: WO2021/233796
PCT Pub. Date: Nov. 25, 2021

(65) Prior Publication Data
US 2023/0310360 A1     Oct. 5, 2023

Related U.S. Application Data

(60) Provisional application No. 63/027,063, filed on May 19, 2020.

(51) Int. Cl.
   *A61K 31/23*        (2006.01)
   *A23L 2/52*         (2006.01)
   (Continued)

(52) U.S. Cl.
   CPC ................. *A61K 31/23* (2013.01); *A23L 2/52* (2013.01); *A23L 33/12* (2016.08); *A23L 33/40* (2016.08); *A61P 25/28* (2018.01)

(58) Field of Classification Search
   CPC ......... A61K 31/225; A61K 31/23; A61P 9/10; A61P 9/00; A23L 33/12; A23L 2/52
   See application file for complete search history.

(56) References Cited

FOREIGN PATENT DOCUMENTS

JP         06287138 A   *   10/1994
JP       2019500024 W   *   1/2019  ............. A23L 33/12
   (Continued)

OTHER PUBLICATIONS

Cunnane et al: "Can ketones compensate for deteriorating brain glucose uptake during aging? Implications for the risk and treatment of Alzheimer's disease : Brain glucose and ketone uptake in Alzheimer's disease", Annals of the New York Academy of Sciences, vol. 1367, No. 1, pp. 12-20. (Year: 2016).*

(Continued)

*Primary Examiner* — Deborah D Carr
(74) *Attorney, Agent, or Firm* — K&L Gates LLP

(57) ABSTRACT

Methods improve cognitive functioning, for example, at least one of episodic memory, executive function, or language skills; supporting memory and/or recall; providing energy and/or ketones to the brain; and/or preventing and/or treating mild cognitive impairment (MCI) in an individual. A composition comprising medium chain triglycerides (MCTs) can be administered to the individual in a daily dosage providing from about 15 g to about 45 g MCTs. The MCTs can include from about 51 wt % to about 90 wt % of octanoic acid. The daily dose can be provided in at least two servings, for example, 2 or 3 servings. Each serving can provide about 15 g MCTs and can include octanoic acid and decanoic acid in a weight ratio of, for example, about (Continued)

| | PLACEBO (n=43) | | | | ACTIVE (n=39) | | | | | |
| | PRE | | POST | | PRE | | POST | | | Partial |
| | Mean | SD | Mean | SD | Mean | SD | Mean | SD | *p*-value[a] | η² |
|---|---|---|---|---|---|---|---|---|---|---|
| EPISODIC MEMORY | | | | | | | | | | |
| RL/RI-16 - Trial 1 Free recall (/16) | 6.4 | 2.2 | 6.6 | 2.2 | 6.5 | 2.0 | 7.5 | 2.3 | 0.054[a]/0.047[b] | 0.046 |
| RL/RI-16 - Total Free recall (/48) | 23.8 | 6.1 | 23.6 | 6.8 | 24.4 | 6.0 | 25.7 | 6.6 | 0.118 | 0.031 |
| RL/RI-16 - Total recall (/48) | 43.1 | 5.1 | 40.6 | 6.4 | 43.3 | 4.9 | 42.6 | 4.6 | 0.070 | 0.041 |
| BVMT-R - Trial 1 (/12) | 3.7 | 2.0 | 4.6 | 2.1 | 3.1 | 2.1 | 4.6 | 2.4 | 0.647 | 0.003 |
| BVMT-R - Total (/36) | 15.9 | 6.2 | 18.1 | 6.3 | 16.2 | 6.8 | 18.8 | 7.3 | 0.734 | 0.002 |
| EXECUTIVE FUNCTION | | | | | | | | | | |
| Verbal fluency – Letters (total correct) | 29.1 | 8.1 | 29.4 | 8.0 | 31.6 | 10.4 | 32.6 | 11.9 | 0.402 | 0.009 |
| Verbal fluency- Categories (total correct) | 32.5 | 6.2 | 31.5 | 7.5 | 33.4 | 7.8 | 35.3 | 7.8 | 0.005[a]/0.024[b] | 0.098 |
| Trail Making – Switching (sec) | 130 | 49 | 131 | 59 | 124 | 56 | 120 | 53 | 0.664 | 0.002 |
| Trail Making - Total errors, all conditions | 1.7 | 2.4 | 2.5 | 3.7 | 2.7 | 4.1 | 1.8 | 2.5 | 0.020[a]/0.017[b] | 0.067 |
| Stroop- Inhibition (sec) | 85 | 28 | 85 | 31 | 79 | 25 | 77 | 21 | 0.535 | 0.005 |
| Stroop - Inhibition/switching (sec) | 99 | 38 | 102 | 50 | 87 | 29 | 84 | 26 | 0.257 | 0.017 |
| Stroop - Total errors, all conditions | 9.0 | 8.1 | 7.4 | 5.4 | 5.9 | 5.4 | 3.9 | 5.3 | 0.042[a]/0.113[b] | 0.053 |
| ATTENTION AND PROCESSING SPEED | | | | | | | | | | |
| Trail Making – Visual scanning (sec) | 28 | 9 | 29 | 8 | 29 | 10 | 29 | 9 | 0.919 | 0.000 |
| Trail Making – Number sequencing (sec) | 52 | 22 | 49 | 26 | 49 | 26 | 43 | 20 | 0.350 | 0.011 |
| Trail Making – Letter sequencing (sec) | 49 | 18 | 51 | 20 | 55 | 30 | 55 | 34 | 0.771 | 0.001 |
| Stroop - Color naming (sec) | 35 | 6 | 35 | 7 | 36 | 9 | 35 | 9 | 0.090 | 0.037 |
| Stroop - Reading (sec) | 26 | 4 | 26 | 5 | 26 | 7 | 26 | 6 | 0.473 | 0.007 |
| LANGUAGE | | | | | | | | | | |
| Boston Naming Test - total correct responses (/60) | 53.2 | 3.6 | 53.0 | 4.8 | 53.7 | 4.1 | 54.8 | 3.9 | ‡ 0.018[a]/0.033[b] | 0.069 | p-values are for between-group differences after (POST) the six-month intervention with the pre-intervention value as a covariable.
‡ Results from multiple regressions are reported as significant mean differences at any given value of the covariable.
[a] Quade transformation
[b] Only pre-intervention score as a covariable.
[c] Sex, age, education, ApoE4 status, amnestic status added as covariables in the model.
RL/RI-16, 16-item free/cued word learning and recall test; BVMT-R, Brief visuospatial memory test – Revised; Stroop, Stroop color-word interference test; Partial η² – measure of effect size.

60:about 40. The individual can be 65 years or older and/or have mild cognitive impairment (MCI).

12 Claims, 18 Drawing Sheets

(51) Int. Cl.
| | |
|---|---|
| *A23L 33/00* | (2016.01) |
| *A23L 33/12* | (2016.01) |
| *A61P 25/28* | (2006.01) |

(56) References Cited

FOREIGN PATENT DOCUMENTS

| WO | 2015121218 | 8/2015 | | |
|---|---|---|---|---|
| WO | WO-2015121218 A1 * | 8/2015 | ........... | A61K 31/185 |
| WO | 2017093060 | 6/2017 | | |
| WO | WO-2017093060 A1 * | 6/2017 | ............. | A23L 33/12 |
| WO | WO-2018207921 A1 * | 11/2018 | ............... | A23D 9/00 |
| WO | 2020011747 | 1/2020 | | |
| WO | WO-2020011747 A1 * | 1/2020 | ........... | A23C 9/1528 |
| WO | 2020193291 | 10/2020 | | |

OTHER PUBLICATIONS

Fortier et al., "A ketogenic drink improves brain energy and some measures of cognition in mild cognitive impairment", Alzheimer's & Dementia, vol. 15, pp. 625-634. (Year: 2019).*

Henderson et al., "Study of the ketogenic agent AC-1202 in mild to moderate Alzheimer's disease: a randomized, double-blind, placebo-controlled, multicenter trial" Nutrition & Metabolism, vol. 6, Article No. 31, pp. 1-25 (Year: 2009).*

Cunnane et al. "Can ketones compensate for deteriorating brain glucose uptake during aging? Implications for the risk and treatment of Alzheimer's disease" Annals of the New York Academy of Sciences, 2016, vol. 1367, pp. 12-20.

* cited by examiner

FIG. 1

| | PLACEBO (n=43) | | | | ACTIVE (n=39) | | | | p-value[a] | Partial $\eta^2$ |
| | PRE | | POST | | PRE | | POST | | | |
| | Mean | SD | Mean | SD | Mean | SD | Mean | SD | | |
|---|---|---|---|---|---|---|---|---|---|---|
| EPISODIC MEMORY | | | | | | | | | | |
| RL/RI-16 - Trial 1 Free recall (/16) | 6.4 | 2.2 | 6.6 | 2.2 | 6.5 | 2.0 | 7.5 | 2.3 | 0.054[a]/0.047[b] | 0.046 |
| RL/RI-16 - Total Free recall (/48) | 23.8 | 6.1 | 23.6 | 6.8 | 24.4 | 6.0 | 25.7 | 6.6 | 0.118 | 0.031 |
| RL/RI-16 - Total recall (/48) | 43.1 | 5.1 | 40.6 | 6.4 | 43.3 | 4.9 | 42.6 | 4.6 | 0.070 | 0.041 |
| BVMT-R - Trial 1 (/12) | 3.7 | 2.0 | 4.6 | 2.1 | 3.1 | 2.1 | 4.6 | 2.4 | 0.647 | 0.003 |
| BVMT-R – Total (/36) | 15.9 | 6.2 | 18.1 | 6.3 | 16.2 | 6.8 | 18.8 | 7.3 | 0.734 | 0.002 |
| EXECUTIVE FUNCTION | | | | | | | | | | |
| Verbal fluency – Letters (total correct) | 29.1 | 8.1 | 29.4 | 8.0 | 31.6 | 10.4 | 32.6 | 11.9 | 0.402 | 0.009 |
| Verbal fluency- Categories (total correct) | 32.5 | 6.2 | 31.5 | 7.5 | 33.4 | 7.8 | 35.3 | 7.8 | 0.005[a]/0.024[b] | 0.098 |
| Trail Making – Switching (sec) | 130 | 49 | 131 | 59 | 124 | 56 | 120 | 53 | 0.664 | 0.002 |
| Trail Making - Total errors, all conditions | 1.7 | 2.4 | 2.5 | 3.7 | 2.7 | 4.1 | 1.8 | 2.5 | 0.020[a]/ 0.017[b] | 0.067 |
| Stroop– Inhibition (sec) | 85 | 28 | 85 | 31 | 79 | 25 | 77 | 21 | 0.535 | 0.005 |
| Stroop - Inhibition/switching (sec) | 99 | 38 | 102 | 50 | 87 | 29 | 84 | 26 | 0.257 | 0.017 |
| Stroop - Total errors, all conditions | 9.0 | 8.1 | 7.4 | 5.4 | 5.9 | 5.4 | 3.9 | 5.3 | 0.042[a]/ 0.113[b] | 0.053 |
| ATTENTION AND PROCESSING SPEED | | | | | | | | | | |
| Trail Making – Visual scanning (sec) | 28 | 9 | 29 | 8 | 29 | 10 | 29 | 9 | 0.919 | 0.000 |
| Trail Making – Number sequencing (sec) | 52 | 22 | 49 | 26 | 49 | 26 | 43 | 20 | 0.350 | 0.011 |
| Trail Making – Letter sequencing (sec) | 49 | 18 | 51 | 20 | 55 | 30 | 55 | 34 | 0.771 | 0.001 |
| Stroop - Color naming (sec) | 35 | 6 | 35 | 7 | 36 | 9 | 35 | 9 | 0.090 | 0.037 |
| Stroop - Reading (sec) | 26 | 4 | 26 | 5 | 26 | 7 | 26 | 6 | 0.473 | 0.007 |
| LANGUAGE | | | | | | | | | | |
| Boston Naming Test - total correct responses (/60) | 53.2 | 3.6 | 53.0 | 4.8 | 53.7 | 4.1 | 54.8 | 3.9 | ‡ 0.018[a]/0.033[b] | 0.069 |

FIG. 1 (cont'd)

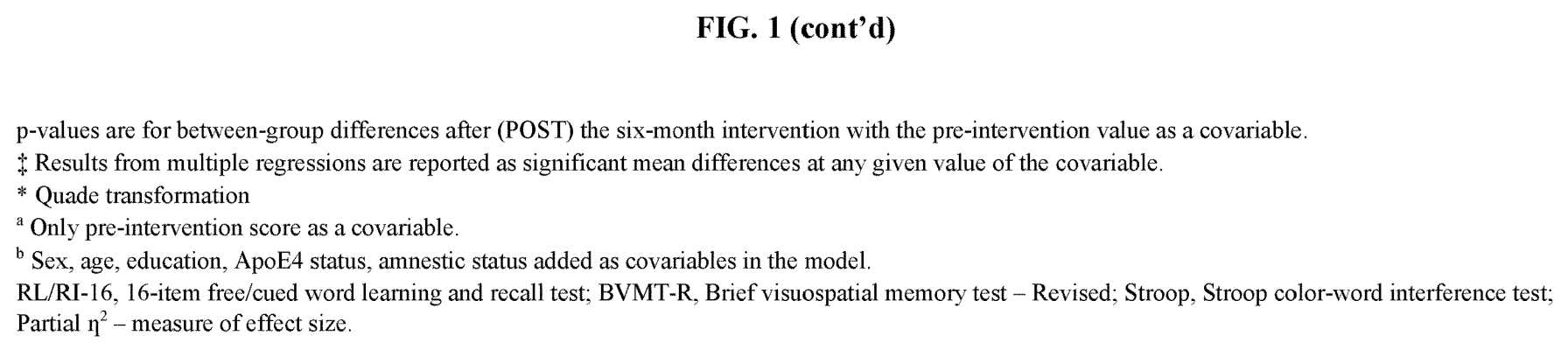

p-values are for between-group differences after (POST) the six-month intervention with the pre-intervention value as a covariable.

‡ Results from multiple regressions are reported as significant mean differences at any given value of the covariable.

\* Quade transformation

[a] Only pre-intervention score as a covariable.

[b] Sex, age, education, ApoE4 status, amnestic status added as covariables in the model.

RL/RI-16, 16-item free/cued word learning and recall test; BVMT-R, Brief visuospatial memory test – Revised; Stroop, Stroop color-word interference test; Partial $\eta^2$ – measure of effect size.

FIG. 2

| Z Score | PLACEBO (N=43) | | | | ACTIVE (N=39) | | | | p-value[a] | Partial $\eta^2$ |
|---|---|---|---|---|---|---|---|---|---|---|
| | PRE | | POST | | PRE | | POST | | | |
| | Mean | SD | Mean | SD | Mean | SD | Mean | SD | | |
| Episodic Memory | | | | | | | | | | |
| RL/RI-16 - Trial 1 Free Recall | -0.84 | 1.09 | -0.74 | 1.13 | -0.77 | 0.89 | -0.26 | 1.04 | 0.042[a]/0.024[b] | 0.051 |
| RL/RI-16 - Total Free Recall | -0.98 | 1.14 | -1.02 | 1.28 | -0.91 | 0.93 | -0.65 | 1.10 | 0.120 | 0.030 |
| RL/RI-16 - Total Recall | -0.77 | 0.88 | -0.80 | 1.00 | -0.72 | 0.89 | -0.53 | 0.93 | 0.146 | 0.027 |
| Executive function | | | | | | | | | | |
| Verbal Fluency – Letter | -0.56 | 0.83 | -0.52 | 0.80 | -0.33 | 1.05 | -0.21 | 1.18 | 0.410 | 0.009 |
| Verbal Fluency- Categories | -0.12 | 0.83 | -0.23 | 0.93 | -0.05 | 0.93 | 0.22 | 0.95 | 0.005[a]/0.018[c] | 0.098 |
| Trail Making – Switching | -0.15 | 1.02 | -0.12 | 1.25 | -0.09 | 1.24 | 0.07 | 1.11 | 0.575 | 0.004 |
| Trail Making- Errors, Switching | 0.26 | 0.60 | 0.03 | 0.93 | 0.08 | 0.95 | 0.25 | 0.66 | 0.043[a]/0.047[c] | 0.052 |
| Stroop– Inhibition | -0.51 | 1.17 | -0.40 | 1.21 | -0.22 | 1.12 | -0.14 | 0.99 | 0.953 | 0.000 |
| Stroop - Inhibition/Switching | -0.70 | 1.31 | -0.58 | 1.19 | -0.21 | 1.11 | -0.12 | 1.06 | 0.369 | 0.007 |
| Stroop - Errors inhibition | -0.07 | 1.08 | -0.02 | 0.97 | 0.18 | 0.83 | 0.45 | 0.73 | 0.046[a]/0.092[c] | 0.051 |
| Stroop - Errors inhibition/Switching | -0.48 | 1.26 | -0.36 | 1.06 | 0.02 | 0.92 | 0.38 | 0.81 | 0.007[a]/0.011[c] | 0.089 |
| Language | | | | | | | | | | |
| Boston –Spontaneous responses | -1.85 | 1.29 | -1.64 | 1.31 | -1.58 | 1.23 | -1.28 | 1.26 | 0.416 | 0.008 | p-values are for between-group differences after (POST) the six-month intervention with the pre-intervention value as a covariable.

‡ Results from multiple regressions are reported as significant mean differences at any given value of the covariable.

* Quade transformation

[a] Only pre-intervention score as a covariable.

[b] ApoE4 and amnestic status added as covariables in the model.

[c] Sex, education, ApoE4 status, amnestic status added as covariables in the model.

RL/RI-16, 16-item free/cued word learning and recall test; Stroop, Stroop color-word interference test; Partial $\eta^2$ – measure of effect size.

FIG. 3

| | PLACEBO | | | | ACTIVE | | | | |
| | PRE | | POST | | PRE | | POST | | p-value |
| | Mean | SD | Mean | SD | Mean | SD | Mean | SD | |
| --- | --- | --- | --- | --- | --- | --- | --- | --- | --- |
| Beta-hydroxybutyrate (µM) | 137 | 116 | 106 | 100 | 127 | 125 | 401 | 303 | 0.000* |
| Acetoacetate (µM) | 96 | 79 | 69 | 59 | 92 | 62 | 205 | 136 | 0.000 |
| Total ketones (µM) † | 252 | 197 | 175 | 155 | 241 | 190 | 606 | 425 | 0.000* |
| Glucose (mM) | 4.8 | 0.6 | 5.0 | 0.4 | 5.0 | 0.8 | 5.4 | 0.7 | 0.024 |
| Glycated hemoglobin (%) | 5.6 | 0.5 | 5.6 | 0.4 | 5.7 | 0.4 | 5.6 | 0.3 | 0.487 |
| Total cholesterol (mM) | 5.0 | 1.2 | 4.9 | 1.2 | 4.8 | 1.0 | 5.2 | 1.0 | 0.013 |
| High-density lipoprotein (mM) | 1.7 | 0.4 | 1.6 | 0.5 | 1.5 | 0.4 | 1.4 | 0.4 | 0.493 |
| Low-density lipoprotein (mM) | 2.8 | 1.1 | 2.8 | 1.3 | 2.8 | 0.9 | 3.0 | 0.9 | 0.612 |
| Triglycerides (mM) | 1.1 | 0.5 | 1.5 | 0.7 | 1.2 | 0.6 | 1.7 | 0.8 | 0.111 |
| Thyroid stimulating hormone (mUI/L) | 2.1 | 1.2 | 2.2 | 1.4 | 2.3 | 0.8 | 2.4 | 1.0 | 0.582 |
| Alanine transaminase (UI/L) | 18 | 6 | 17 | 5 | 21 | 8 | 24 | 12 | 0.065* |
| Aspartate transaminase (UI/L) | 21 | 4 | 20 | 5 | 22 | 5 | 24 | 5 | 0.030 |
| C-Reactive protein (mg/L) | 2.9 | 2.0 | 2.9 | 2.0 | 3.2 | 3.0 | 2.9 | 1.6 | 0.282 |
| Creatinine (µM) | 74 | 14 | 72 | 15 | 78 | 22 | 78 | 24 | 0.576 |
| Glomerular filtration rate (mL/min/1,73m$^2$) | 79 | 11 | 80 | 11 | 78 | 16 | 79 | 16 | 0.498 |
| Chloride (mM) | 102 | 3 | 102 | 2 | 102 | 2 | 102 | 2 | 0.883 |
| Sodium (mM) | 141 | 2 | 141 | 2 | 141 | 2 | 141 | 2 | 0.551 |
| Potassium (mM) | 4.3 | 0.4 | 4.1 | 0.4 | 4.2 | 0.4 | 4.0 | 0.3 | 0.635 |
| Albumin (g/L) | 43 | 2 | 42 | 5 | 43 | 2 | 43 | 2 | 0.055 |
| Cysteine (µM) | 274 | 37 | 276 | 43 | 279 | 42 | 275 | 38 | 0.749 |
| Homocysteine (µM) | 26 | 4 | 26 | 4 | 28 | 4 | 27 | 7 | 0.658 |
| Body mass index (kg/m$^2$) | 26.1 | 4.2 | 26.3 | 4.0 | 27.9 | 3.9 | 27.1 | 6.8 | 0.503 | p-values are for between-group differences post-intervention with pre-intervention values as a covariable.

*Quade Transformation.

† BHB and AcAc combined.

FIG. 9

| Raw Score | PLACEBO (n=38) | | | | ACTIVE (n=33) | | | | p-value |
|---|---|---|---|---|---|---|---|---|---|
| | PRE | | POST | | PRE | | POST | | |
| | Mean | SD | Mean | SD | Mean | SD | Mean | SD | |
| Age | 72.5 | 7.0 | | | 70.9 | 6.8 | | | 0.319 |
| Education (y) | 12.8 | 3.4 | | | 13.0 | 3.3 | | | 0.797 |
| EPISODIC MEMORY | | | | | | | | | |
| RL/RI16 - Trial 1 Free recall (/16) | 6.3 | 2.0 | 6.5 | 2.3 | 6.7 | 1.9 | 7.8 | 2.3 | 0.028 |
| RL/RI16 - Total Free recall (/48) | 23.5 | 5.9 | 23.3 | 7.1 | 24.9 | 6.2 | 26.8 | 6.3 | 0.043 |
| RL/RI16 - Total recall (/48)[c] | 42.9 | 5.3 | 40.2 | 6.7 | 43.7 | 4.7 | 43.0 | 4.6 | 0.109 |
| EXECUTIVE FUNCTION | | | | | | | | | |
| Verbal fluency- Categories (total correct) | 32.7 | 6.5 | 31.6 | 7.9 | 34.5 | 7.9 | 36.1 | 7.9 | 0.014 |
| Trail Making - total errors, all conditions | 1.7 | 2.5 | 2.6 | 3.9 | 2.5 | 3.5 | 1.6 | 1.5 | 0.024 |
| Stroop - Total errors, all conditions | 8.9 | 8.5 | 7.2 | 5.5 | 5.6 | 4.1 | 3.3 | 3.1 | 0.002 |
| LANGUAGE | | | | | | | | | |
| Boston Naming Test, total correct responses (/60) | 53.0 | 3.6 | 52.8 | 5.0 | 53.9 | 4.3 | 55.0 | 4.0 | 0.028 |

Protocol compliance was defined as those consuming ≥80% of the prescribed dose.

FIG. 10

| | PLACEBO (n=31) | | | | ACTIVE (n=34) | | | | |
| | PRE | | POST | | PRE | | POST | | |
| | Mean | SD | Mean | SD | Mean | SD | Mean | SD | p-value |
|---|---|---|---|---|---|---|---|---|---|
| Age | 72.4 | 6.9 | | | 71.7 | 6.6 | | | 0.692 |
| Education (y) | 12.9 | 3.4 | | | 12.8 | 3.2 | | | 0.923 |
| EPISODIC MEMORY | | | | | | | | | |
| RL/RI-16 - Immediate recall (/16) | 14.5 | 1.3 | 14.0 | 2.0 | 14.6 | 1.5 | 14.8 | 1.5 | 0.06 |
| RL/RI-16 - Trial 1 Free recall (/16) | 6.2 | 2.3 | 6.4 | 2.1 | 6.2 | 1.8 | 7.4 | 2.3 | 0.05 |
| RL/RI-16 - Total Free recall (/48) | 22.2 | 5.8 | 22.5 | 6.5 | 23.6 | 5.8 | 25.2 | 6.8 | 0.19 |
| RL/RI-16 - Total recall (/48)[c] | 41.5 | 5.3 | 39.1 | 6.5 | 42.7 | 5.1 | 42.2 | 4.6 | 0.05 |

The RL-RI-16 data are shown as raw scores.

FIG. 11

| | PLACEBO (n=32) | | | | ACTIVE (n=28) | | | | p-value |
| | PRE | | POST | | PRE | | POST | | |
| | Mean | SD | Mean | SD | Mean | SD | Mean | SD | |
|---|---|---|---|---|---|---|---|---|---|
| Age | 72.9 | 7.1 | | | 71.8 | 7.4 | | | 0.545 |
| Education (y) | 12.1 | 3.8 | | | 14.0 | 2.9 | | | 0.032 |
| EPISODIC MEMORY | | | | | | | | | |
| RL/RI16 – Immediate recall (/16) | 14.9 | 1.2 | 14.9 | 1.3 | 15.0 | 1.1 | 15.0 | 1.4 | 0.81 |
| RL/RI16 - Trial 1 Free recall (/16) | 6.9 | 2.2 | 6.9 | 2.1 | 6.6 | 2.0 | 7.6 | 1.6 | 0.15 |
| RL/RI16 - Total Free recall (/48) | 24.6 | 6.1 | 24.8 | 6.1 | 24.7 | 5.5 | 26.2 | 4.9 | 0.22 |
| RL/RI16 - Total recall (/48)[c] | 43.6 | 5.5 | 41.6 | 5.4 | 43.5 | 4.9 | 43.3 | 3.8 | 0.04 |
| EXECUTIVE FUNCTION | | | | | | | | | |
| Verbal fluency- Categories (total correct) | 32.4 | 5.7 | 32.2 | 6.9 | 33.6 | 8.4 | 36.1 | 8.0 | 0.02 |
| Trail Making - total errors, all conditions | 1.7 | 2.7 | 2.0 | 3.2 | 1.6 | 2.0 | 1.3 | 1.0 | 0.16 |
| Stroop - Total errors. all conditions | 9.2 | 8.2 | 7.4 | 5.3 | 4.8 | 3.8 | 3.1 | 3.0 | 0.01 |
| LANGUAGE | | | | | | | | | |
| Boston Naming Test - total correct responses (/60) | 52.8 | 3.8 | 52.8 | 5.2 | 53.7 | 4.3 | 55.3 | 3.8 | 0.01 |

The cognitive test scores are shown as raw data.

FIG. 12

|  | PLACEBO (n=9) | | | | ACTIVE (n=10) | | | | |
|  | PRE | | POST | | PRE | | POST | | |
|  | Mean | SD | Mean | SD | Mean | SD | Mean | SD | p-value |
|---|---|---|---|---|---|---|---|---|---|
| Age | 73 | 6 | | | 71 | 7 | | | 0.369 |
| Education (y) | 15 | 2 | | | 11 | 3 | | | 0.005 |
| EPISODIC MEMORY | | | | | | | | | |
| RL/RI16 – Immediate recall (/16) | 14.2 | 1.0 | 13.3 | 2.0 | 13.8 | 1.8 | 14.6 | 1.8 | 0.030 |
| RL/RI16 - Trial 1 Free recall (/16) | 5.1 | 1.8 | 5.7 | 2.5 | 6.4 | 2.2 | 7.7 | 3.5 | 0.868 |
| RL/RI16 - Total Free recall (/48) | 22.0 | 6.2 | 20.6 | 8.5 | 24.1 | 7.8 | 25.4 | 10.0 | 0.510 |
| RL/RI16 - Total recall (/48)[C] | 42.0 | 3.7 | 38.7 | 9.1 | 43.2 | 5.1 | 42.0 | 4.9 | 0.895 |
| EXECUTIVE FUNCTION | | | | | | | | | |
| Verbal fluency- Categories (total correct) | 32.4 | 7.5 | 30.0 | 9.2 | 32.6 | 6.8 | 32.2 | 6.6 | 0.048 |
| Trail Making - total errors, all conditions | 1.2 | 1.0 | 4.4 | 4.9 | 6.1 | 6.3 | 3.7 | 4.5 | 0.017 |
| Stroop - Total errors, all conditions | 9.9 | 8.6 | 8.2 | 6.3 | 9.4 | 7.8 | 6.4 | 9.3 | 0.434 |
| LANGUAGE | | | | | | | | | |
| Boston Naming Test - total correct responses (/60) | 54.0 | 2.7 | 53.6 | 4.2 | 54.1 | 3.9 | 53.7 | 4.4 | 0.640 |

The cognitive test scores are shown as raw data.

FIG. 13

|  | Placebo (N=43) | | | | Active (N=39) | | | | |
|  | PRE | | POST | | PRE | | POST | | |
|  | Mean | SD | Mean | SD | Mean | SD | Mean | SD | p-value |
|---|---|---|---|---|---|---|---|---|---|
| Episodic Memory | -0.74 | 0.86 | -0.65 | 1.01 | -0.74 | 0.95 | -0.53 | 0.97 | 0.629 |
| Working Memory | -0.70 | 0.79 | -0.75 | 0.75 | -0.89 | 0.75 | -0.77 | 0.64 | 0.362 |
| Executive Function | -0.44 | 0.74 | -0.39 | 0.88 | -0.21 | 0.84 | -0.16 | 0.78 | 0.869 |
| Speed processing and Attention | 0.11 | 0.51 | 0.17 | 0.62 | 0.04 | 0.74 | 0.12 | 0.71 | 0.907 |
| Language | -1.85 | 1.29 | -1.64 | 1.31 | -1.58 | 1.23 | -1.28 | 1.26 | 0.416 |

Placebo (POST *vs.* PRE): $p = 0.63$
* Active (POST *vs.* PRE): $p = 0.001$
* $\Delta$PLACEBO *vs.* $\Delta$ACTIVE: $p = 0.001$

FIG. 16

| | Test Name | Description | Type of cognitive function | Test sub-type |
|---|---|---|---|---|
| 1. | Free and Cued Recall* | 16-item Free and Cued Recall | Episodic memory<br><br>Working memory | Immediate recall<br><br>3 trials + a delayed trial<br><br>Each trial without and with a cue |
| 2. | Brief Visuospatial Memory (BVMT-R) | Visuospatial memory | Episodic memory | 3 trials + a delayed trial |
| 3. | Trail making tests | Trail Making<br><br>D-KEFS | Attention<br><br>Executive function<br><br>Processing speed | 5 conditions (scanning, number sequence, letter sequence, switching, motor speed)<br><br>Number of errors |
| 4. | Color-Word Interference Test | Stroop<br><br>D-KEFS | Executive function<br><br>Processing speed | 4 conditions (color naming, reading, inhibition, inhibition switching); errors counted |
| 5. | Letters and category | Verbal fluency<br><br>D-KEFS | Executive function | 3 letters<br><br>2 categories<br><br>Switching category |
| 6. | Naming test | Boston | Language | 60 items, with contextual and phonetic cues |

FIG. 17

| | TEST | Cognitive domain | Sub-tests | Improvement / measure | BENEFIC 1+2 N= 44 placebo, n=39 MCT |
|---|---|---|---|---|---|
| 1 | 16-item free and cued recall | Episodic memory | Trial 1 | ↑ words recalled | MCT: +1 word |
| | | | Trials 1+2+3 combined | ↑ words recalled | Placebo: -2.5 words MCT: -0.7 word |
| | | | Delayed | ↑ words recalled | |
| 2 | Visuo spatial memory | Episodic memory | Trial 1 | ↑ copied drawing | |
| | | | Trials 1+2+3 | ↑ copied drawing | |
| 3 | Trail making | Processing speed | Scanning | ↓ time | |
| | | | Letter | ↓ time | |
| | | | Number | ↓ time | |
| | | attention | Errors | ↓ errors | Placebo: +0.8 errors MCT: -0.9 errors |
| 4 | Stroop | Executive function | Color naming | ↓ time | MCT: -1 sec |
| | | | Reading vs Switching | ↑ normalized performance | Placebo: -0.3 Z-score MCT: +0.3 Z-score |
| 5 | Verbal fluency | Executive function | Letter | ↑ words | |
| | | | Category | ↑ words | Placebo: -1 word; MCT: +2 words |
| 6 | Boston naming | Language | No cue | ↑ correct answers | |
| | | | Correct | ↑ correct answers | MCT: +1.1 correct answers |

Parametric ANCOVA analysis: MCT vs placebo, differences POST treatment accounting for PRE values, and controlled for age and education.

Significant differences presented (normalized score; $p<0.05$)

FIG. 18

| # | TEST | Cognitive domain | sub-test | Improvement / measure | BENEFIC 1+2 (44 placebo, 39 MCT) | Benefic 1 (Fortier 2019) Placebo N=20 | MCT N=19 | delta | Benefic 2 Placebo N=24 | MCT N=20 | delta |
|---|------|------------------|----------|------------------------|----------------------------------|----------------------------------------|----------|-------|-------------------------|----------|-------|
| 1 | 16-item free and cued recall | Episodic memory | Trial 1 | ↑ words recalled | MCT: +1 word* | | +1.3 words | | | | |
| | | | 1+2+3 total | ↑ words recalled | Placebo: -2.5 word MCT: -0.7 word | | | | -2.3 words | (↑) | |
| | | | Delayed | ↑ words recalled | | -1.3 words | | | | | (*) |
| 2 | Visuo-spatial memory | Episodic memory | Trial 1 | ↑ drawings copied | | (↑) | +1.3 points | | | +1.5 points | |
| | | | 1+2+3 | ↑ drawings copied | | (↑) | (↑) | | | +2.3 points | |
| | | Processing speed | Scanning | ↓ time | | +4 sec | | | | | |
| | | | Letter | ↓ time | | | -4 sec | | -4 sec | | |
| | | | Number | ↓ time | | | | | | -4 sec | |
| 3 | Trail making | Attention | Errors | ↓ errors | Placebo: +0.8 errors MCT: -0.9 errors | | | | (↑) | | (*) |

FIG.18 Cont'd

| # | Test | Domain | Subtest | Direction | | | (↑) | |
|---|------|--------|---------|-----------|--|--|-----|--|
| 4 | Stroop | Executive function | Color naming | ↓ time | MCT: -1 sec | | (↑) | |
| | | | Reading vs Switching | ↑ normalized performance | Placebo: -0.3 Z-score MCT: +0.3 Z-score | | | |
| 5 | Verbal fluency | Executive function | Letter | ↑ words | MCT: -1sec | | | +3.2 words |
| | | | Category | ↑ words | Placebo: -1 word MCT: +2 words | -2.1 words | | +3.4 words ** |
| | | | No cue | ↑ correct answers | | | | +1.4 correct answers |
| 6 | Boston naming | Language | Correct | ↑ correct answers | MCT: +1.1 correct answers -1.3 correct answers | +1.0 correct answers ** | | |

Significant differences presented $p < 0.05$ (raw data and normalised score both significant, except where specified*); (Trend) presented (↑) or (↓)

Benefic 1+2: parametric ANCOVA analysis MCT vs placebo differences POST accounting for PRE values, controlled for age and education Benefic 1 and Benefic 2 separated analysis: nonparametric intragroup difference after treatment (pre vs post);

** Delta: significant difference between group in Benefic 1 or Benefic 2 (delta placebo vs delta MCT)

MCT FORMULATIONS FOR IMPROVING COGNITIVE FUNCTIONS

CROSS REFERENCE TO RELATED APPLICATIONS

The present application is a National Stage of International Application No. PCT/EP2021/062908, filed on May 17, 2021, which claims priority to U.S. Provisional Patent Application No. 63/027,063, filed on May 19, 2020, the entire contents of which are being incorporated herein by reference.

BACKGROUND

The present disclosure generally relates to compositions comprising medium chain triglycerides (MCTs) and further comprising a food matrix into which at least a portion of the MCTs are formulated. The composition can improve cognitive functioning, support memory and/or recall, provide energy and/or ketones to the brain, and/or prevent and/or treat mild cognitive impairment (MCI).

The two main ketones, beta-hydroxybutyrate (BHB) and acteto actetate (AcA), represent an important alternative source of energy for extrahepatic tissues like brain, heart or skeletal muscle. Moreover, accumulating evidence suggests that ketones might also have a signaling role, either direct or indirect. Products aimed at increasing blood ketones have potential therapeutic benefits in several conditions including, but not limited to, epilepsy, neurological and neurodegenerative diseases, heart failure, inborn errors of metabolism, obesity, type 2 diabetes, cancer, exercise performance, and nonalcoholic fatty liver disease (NAFLD) such as nonalcoholic steatohepatitis (NASH).

BHB and AcA are actively transported to the brain by the monocarboxylic transporter 1 (MCT1), resulting in brain levels directly proportional to their blood concentrations. Therefore, products that provide a more sustained plasma level of ketones are anticipated to have a longer effect (longer plasma ketones half-life T' 112) compared to products that raise blood ketones for a shorter time span (shorter half-life).

Medium-chain triglycerides (MCTs) are efficient ketone precursors when administered by oral bolus. They are rapidly digested, and the resultant free medium chain fatty acids (MCFAs) are absorbed efficiently by the portal vein to reach the liver where they are extensively metabolized to ketones, bypassing the normal long-chain fatty acid digestion and absorption processes. Their specific formulation can affect ketogenesis efficiency and gastrointestinal tolerability.

Brain energy rescue is a potential strategy to reduce cognitive decline in mild cognitive impairment (MCI) and Alzheimer's disease (AD). Impairment of some particular cognitive functions, such as episodic memory and language skills, are predictive of MCI and AD. In those at increased risk of early- or late-onset AD, brain glucose uptake is already lower before the onset of the mild cognitive deficit associated with MCI. Hence, a pre-symptomatic brain energy (glucose) deficit of about 10% is present which is sufficient to be contributing to cognitive decline in MCI.

SUMMARY

The present inventors surprisingly and unexpectedly discovered that dietary ketogenic interventions such as a medium chain triglyceride supplement (kMCT) significantly improved some particular cognitive functions, including episodic memory and language skills, both statistically and clinically, indicating a mechanistic link between improved cognitive function and improved brain energy status by ketones.

Accordingly, in a non-limiting embodiment, the present disclosure provides a method of improving cognitive functioning comprising at least one of episodic memory, executive function, and language skills of an individual. The method may comprise administering to the individual a composition comprising medium chain triglycerides (MCTs) in a daily dosage comprising from about 15 g to about 45 g MCTs. The daily dosage may comprise at least two servings of the composition, each serving comprising about 15 g MCTs. The daily dosage may comprise two servings of the composition.

The MCTs may comprise from 51 wt % to 90 wt % of octanoic acid. The MCTs may comprise from 51 wt % to 70 wt % of octanoic acid. The MCTs may comprise from 71 wt % to 90 wt % of octanoic acid. The MCTs may comprise 60 wt % of octanoic acid. The MCTs may further comprise decanoic acid.

The composition may be administered to the individual for at least about 6 months.

The individual can be 65 years or older. The individual may have mild cognitive impairment (MCI). The individual suffers from at least one of deficit in memory, impaired thinking skill comprising inability to make sound decisions and poor judgment, depression, or anxiety. The individual can have or suffer from a brain energy deficiency condition or disease, neurological condition, and/or cognitive impairment.

The composition can further comprise at least one of pyridoxine (vitamin B6), folic acid (vitamin B9), or cobalamin (vitamin B12).

The composition can further comprise proteins in a weight ratio of at least 0.1 g protein/1.0 g of the MCTs. The composition further comprises proteins in a weight ratio of at least 0.4 g protein/1.0 g of the MCTs. Each serving of the composition can comprise about 6.5 g of proteins.

The composition can optionally further comprise (i) carbohydrates in a weight ratio of at least 0.1 g carbohydrate/1.0 g of the MCTs, and/or (ii) lipids, other than the MCTs, in a weight ratio of at least 0.1 g lipids/1.0 g of the MCTs.

The composition can be in a form selected from the group consisting of a beverage, mayonnaise, salad dressing, margarine, low-fat spread, dairy product, cheese spread, processed cheese, dairy dessert, flavoured milk, cream, fermented milk product, cheese, butter, condensed milk product, ice cream mix, soya product, pasteurised liquid egg, bakery product, confectionary product, confectionary bar, chocolate bar, high fat bar, liquid emulsion, spray-dried powder, freeze-dried powder, UHT pudding, pasteurised pudding, gel, jelly, yoghurt, a food with a fat-based or water-containing filling, and combinations thereof.

The composition may be an oral nutritional composition, a nutritional supplement, an oral nutritional supplement, a medical food, a food supplement, a food product, or a food for special medical purpose (FSMP).

The composition may be in a form of a solid powder, a powdered stick, a capsule, or a solution.

In other embodiments, the composition is used in a method of supporting memory and/or recall in an individual; a method of providing energy and/or ketones to the brain of an individual; or a method of preventing and/or treating mild cognitive impairment (MCI) in an individual.

In some embodiments, the compositions can be administered to an individual having a condition selected from the group consisting of epilepsy, a neurological disease, a neurodegenerative disease, heart failure, inborn errors of metabolism, obesity, types 2 diabetes, nonalcoholic fatty liver disease (NAFLD), nonalcoholic steatohepatitis (NASH), cancer, a brain energy deficiency condition, a migraine, a memory disorder, an age-related memory disorder, a brain injury, a stroke, amyloid lateral sclerosis, multiple sclerosis, cognitive impairment, mild cognitive impairment (MCI), cognitive impairment post-intensive care, age-induced cognition impairment, Alzheimer's disease, Parkinson's disease, Huntington's disease, an inherited metabolic disorder, bipolar disorder, schizophrenia, and combinations thereof.

Additional features and advantages are described in, and will be apparent from, the following Detailed Description and the Figures.

BRIEF DESCRIPTION OF DRAWINGS

FIG. 1 is a table showing the raw scores on the neurophysiological tests before (PRE) and after (POST) the intervention according to the experimental example disclosed herein.

FIG. 2 is a table showing normalised Z scores on the neurophysiological tests before (PRE) and after (POST) the intervention according to the experimental example disclosed herein.

FIG. 3 is a table showing clinical chemistry and metabolic parameters before (PRE) and after (POST) the intervention according to the experimental example disclosed herein.

FIG. 6) in with higher scores in Active vs Placebo group (p=0.054, p=0.005, p=0.018, respectively).

FIG. 9 is a table showing the sub-group analysis of protocol-compliant participants.

FIG. 10 is a table showing the sub-group analysis of participants whose MCI included an amnestic component.

FIG. 11 is a table showing the sub-group analysis of ApoE4 (−) participants.

FIG. 12 is a table showing the sub-group analysis of ApoE4 (+) participants.

FIG. 13 is a table showing the Composite Scores for different neurocognitive domain, before (PRE) and after (POST) the intervention according to the experimental example disclosed herein.

FIG. 16 is a table summarizing the cognitive tests according to the experimental example disclosed herein.

FIG. 17 is a table summarizing the significant changes in the cognitive tests according to the experimental example disclosed herein.

FIG. 18 is a table showing more details of the significant changes (FIG. 17) in the cognitive tests according to the experimental example disclosed herein.

DETAILED DESCRIPTION

Definitions

Figures 4, 5, 6:
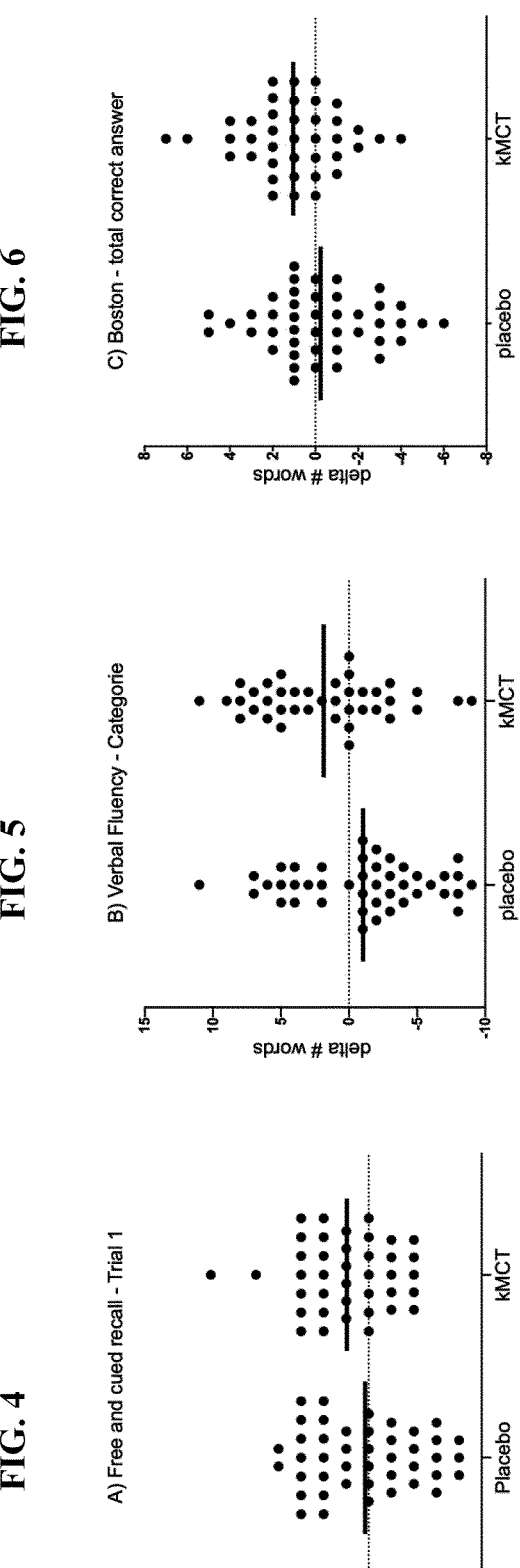
FIGS. 4-6 are plots of the change in raw scores from baseline (0) on the first trial of the RL/RI-16 test (FIG. 4), verbal fluency (categories) test (FIG. 5), and Boston naming test (total correct responses.

Some definitions are provided hereafter. Nevertheless, definitions may be located in the "Embodiments" section below, and the above header "Definitions" does not mean that such disclosures in the "Embodiments" section are not definitions.

All percentages are by weight of the total weight of the composition unless expressed otherwise. Similarly, all ratios are by weight unless expressed otherwise. As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used herein and in the appended claims, the singular form of a word includes the plural, unless the context clearly dictates otherwise. Thus, the references "a," "an" and "the" are generally inclusive of the plurals of the respective terms. For example, reference to "an ingredient" or "a method" includes a plurality of such "ingredients" or "methods." The term "and/or" used in the context of "X and/or Y" should be interpreted as "X," or "Y," or "X and Y." Similarly, "at least one of X or Y" should be interpreted as "X," or "Y," or "both X and Y."

Similarly, the words "comprise," "comprises," and "comprising" are to be interpreted inclusively rather than exclusively. Likewise, the terms "include," "including" and "or" should all be construed to be inclusive, unless such a construction is clearly prohibited from the context. However, the embodiments provided by the present disclosure may lack any element that is not specifically disclosed herein. Thus, a disclosure of an embodiment defined using the term "comprising" is also a disclosure of embodiments "consisting essentially of and "consisting of the disclosed components. "Consisting essentially of means that the embodiment or component thereof comprises more than 50 wt. % of the individually identified components, preferably at least 75 wt. % of the individually identified components, more preferably at least 85 wt. % of the individually identified components, most preferably at least 95 wt. % of the individually identified components, for example at least 99 wt. % of the individually identified components.

Where used herein, the term "example," particularly when followed by a listing of terms, is merely exemplary and illustrative, and should not be deemed to be exclusive or comprehensive. Any embodiment disclosed herein can be combined with any other embodiment disclosed herein unless explicitly indicated otherwise.

"Animal" includes, but is not limited to, mammals, which includes but is not limited to rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage, e.g., an animal benefitting from ketones. While the term "individual" is often used herein to refer to a human, the present disclosure is not so limited. Accordingly, the term "individual" refers to any animal, mammal or human that can benefit from the methods and compositions disclosed herein.

The relative terms "improved," "increased," "enhanced" and the like refer to the properties or effects of the composition containing MCTs in a food matrix (disclosed herein) relative to a composition with an identical formulation except for a lower amount of protein and/or carbohydrate. The terms "maintained" and "sustained" mean that a characteristic of an individual, such as neurologic health, cognitive function or exercise performance, is approximately the same as the average level for the preceding week, the average level for the preceding month, or the average level for the preceding year.

As used herein, the terms "treat" and "treatment" mean to administer a composition as disclosed herein to a subject having a condition in order to lessen, reduce or improve at least one symptom associated with the condition and/or to slow down, reduce or block the progression of the condition. The terms "prevent" and "prevention" mean to administer a composition as disclosed herein to a subject is not showing any symptoms of the condition to reduce or prevent development of at least one symptom associated with the condition.

As used herein, "cognitive function" refers to any mental process that involves symbolic operations, e.g., perception, memory (free recall), executive function, processing speed, attention, speech comprehension, speech generation, language, reading comprehension, creation of imagery, learning, and reasoning, preferably at least memory.

The terms "food," "food product" and "food composition" mean a composition that is intended for ingestion by an individual, such as a human, and that provides at least one nutrient to the individual. The term "food matrix" means the physical structure of the food composition, which can be liquid, solid, or semi-solid in various embodiments. "Food" and its related terms include any food, feed, snack, food supplement, treat, meal substitute, or meal replacement, whether intended for a human or an animal. Animal food includes food or feed intended for any domesticated or wild species. In preferred embodiments, a food for an animal represents a nutritionally complete food or dietary composition, e.g., a pelleted, extruded, or dry food. Examples of such animal foods include extruded pet foods such as foods for dogs and cats.

The term "food for special medical purpose (FSMP)" refers to formula foods specially processed and prepared in order to meet special needs for nutrient or diet of those suffering from food intake restriction, disorder of digestive absorption, disorder of metabolic or certain diseases. Such foods shall be used alone or together with other foods under the guidance of a doctor or clinical nutritionist. FSMP is special dietary food, not medicine, but not ordinarily eaten by normal people. It is specially developed by clinicians and nutritionists based on scientific facts after extensive medical research.

The term "oral nutritional supplement (ONS)" refers to sterile liquids, semi-solids or powders, which provide macro and micro nutrients. They are widely used within the acute and community health settings for individuals who are unable to meet their nutritional requirements through oral diet alone.

A triglyceride (also known as a triacylglycerol or a triacylglyceride) is an ester that is derived from glycerol and three fatty acids. Fatty acids may be either unsaturated or saturated. Fatty acids which are not attached to other molecules are referred to as free fatty acids (FFA).

A medium-chain triglyceride (MCT) is a triglyceride in which all three fatty acid moieties are medium-chain fatty acid moieties. As defined herein, medium-chain fatty acids (MCFA) are fatty acids that have 6 to 14 carbon atoms, preferably 6 to 12 carbon atoms. Medium-chain fatty acids with 8 carbon atoms may be referred to herein as "C8 fatty acids" or "C8." Medium-chain fatty acids with 10 carbon atoms may be referred to herein as "C10 fatty acids" or "C10."

The term "fatty acid moiety" refers to the part of the MCT that originates from a fatty acid in an esterification reaction with glycerol. In a non-limiting example, an esterification reaction between glycerol and only octanoic acid would result in a MCT with octanoic acid moieties. In another non-limiting example, an esterification reaction between glycerol and only decanoic acid would result in a MCT with decanoic acid moieties.

Octanoic acid (also known as caprylic acid) is a saturated fatty acid of the formula $CH_3(CH_2)_6COOH$.

Decanoic acid (also known as capric acid) is a saturated fatty acid of the formula $CH_3(CH_2)_8COOH$.

EMBODIMENTS

An aspect of the present disclosure is a composition comprising medium-chain triglycerides (MCTs). The composition may be an oral nutritional composition, a nutritional supplement, an oral nutritional supplement, a medical food, a food supplement, a food product, or a food for special medical purpose (FSMP). The composition may be in a form of a solid powder, a powdered stick, a capsule, or a solution.

The composition preferably comprises a food matrix into which at least a portion of the MCTs is formulated, and a particularly preferred non-limiting embodiment of the composition is a liquid such as a beverage. The composition can be also in the form of a powder that can be readily dissolved into water prior ingestion. In an embodiment, the composition is administered to an individual in a serving that provides at least about 5 g MCTs, for example at least about 10 g MCTs, for example about 15 g MCTs. In an embodiment, the composition is administered to an individual in a daily dosage comprising from about 15 g to about 45 g MCTs; preferably in a daily dosage comprising about 30 g MCTs. In an embodiment, at least two servings of the composition are administered daily, each serving comprising about 15 g MCTs; preferably two servings of the composition are administered daily, although some embodiments can include more than two servings of the composition.

The MCTs comprise three fatty acid moieties, each of which independently has between 6-12, 6-11, 6-10, 7-12, 7-11, 7-10, 8-12, 8-11 or 8-10 carbon atoms. In an embodiment, at least a portion of the MCTs contain one or more octanoic acid moieties. In an embodiment, at least a portion of the MCTs contain one or more decanoic acid moieties. In an embodiment, at least a portion of the MCTs contain one or more octanoic acid moieties and one or more decanoic acid moieties.

In one embodiment, the MCTs comprises from 51 wt % to 90 wt % of octanoic acid. In one embodiment, the MCTs comprises from 51 wt % to 70 wt % of octanoic acid. In one embodiment, the MCTs comprises from 71 wt % to 90 wt % of octanoic acid. In one embodiment, the MCTs comprises 60 wt % of octanoic acid. In one embodiment, a weight ratio of the octanoic acid and the decanoic acid is 60:40.

The composition may further comprise protein. The protein is preferably in weight ratio relative to the MCTs of at least about 0.1 g protein/1.0 g MCTs, preferably at least about 0.4 g protein/1.0 g MCTs, more preferably at least about 0.8 g protein/1.0 g MCTs, more preferably at least about 1.0 g protein/1.0 g MCTs, even more preferably at least about 1.5 g protein/1.0 g MCTs, most preferably at least about 1.7 g protein/1.0 g MCTs.

Optionally the composition may further comprise carbohydrate and/or other lipids in addition to the MCTs.

If carbohydrate is present, the carbohydrate is preferably in weight ratio relative to the MCTs of at least about 0.3 g carbohydrate/1.0 g MCTs, preferably at least about 1.0 g carbohydrate/1.0 g MCTs, more preferably at least about 2.0 g carbohydrate/1.0 g MCTs, even more preferably at least about 3.0 g carbohydrate/1.0 g MCTs, yet more preferably at least about 4.0 g carbohydrate/1.0 g MCTs, most preferably at least about 4.7 g carbohydrate/1.0 g MCTs.

If lipid other than the MCTs is present, the lipid other than MCTs is preferably in a weight ratio relative to the MCTs of at least about 0.1 g lipid/1.0 g MCTs, at least about 0.2 g lipid/1.0 g MCTs, preferably at least about 0.3 g lipid/1.0 g MCT, at least about 0.4 g lipid/1.0 g MCT, at least about 0.6 g lipid/1.0 g MCT, at least about 0.8 g lipid/1.0 g MCT or at least 1.0 g lipid/1.0 g MCT. In an embodiment, if lipid other than MCTs is present the lipid other than MCT may be present at a ratio lipid other than MCT:MCTs of from 0.1:2.0 to 2.0:1.0, preferably 0.1:1.0 to 1.0:2.0.

The MCTs is preferably 1-50 wt. % of the composition, for example 1-30 wt. %, 1-10 wt. %, 2-10 wt. %, 3-10 wt. %, 4-10 wt. %, 5-10 wt. %, 6-10 wt. %, 7-10 wt. % or 8-10 wt. % of the composition. In an embodiment in which the composition is a liquid, the composition can comprise at least about 40 g MCTs/L, preferably at least about 50 g MCTs/L, more preferably at least about 75 g MCTs/L, even more preferably at least about 100 g MCTs/L, most preferably at least about 120 g MCTs/L. The MCTs can be in the liquid at a level up to about 250 g/L, preferably up to about 200 g MCTs/L, more preferably up to about 175 g MCTs/L, most preferably up to about 150 g MCTs/L.

In an embodiment in which the composition is a liquid, the composition can comprise at least about 52 g protein/L, preferably at least about 60 g protein/L, more preferably at least about 65 g protein/L, most preferably at least about 68 g protein/L. In an embodiment in which the composition is a liquid, the composition can comprise at least about 36 g carbohydrate/L, preferably at least about 50 g carbohydrate/L, more preferably at least about 75 g carbohydrate/L, even more preferably at least about 100 g carbohydrate/L, yet more preferably at least about 150 g carbohydrate/L, most preferably at least about 188 g carbohydrate/L.

Preferably the composition contains one or more natural sources that provide at least a portion of the MCTs. Non-limiting examples of suitable natural sources of MCTs include coconuts, coconut oil, palm kernels, and palm kernel oils. For example, decanoic acid and octanoic acid form about 5-8% and 4-10% of the fatty acid composition of coconut oil, respectively.

Additionally or alternatively, at least a portion of the MCTs may be synthesized by esterification of glycerol with one or more medium-chain fatty acids (MCFA) with a tail of 6 to 12 carbon atoms. For example, a homotriglyceride comprising three fatty acid moieties each with 8 carbon atoms can be synthesized by esterification of glycerol with C8 fatty acids (e.g., octanoic acid), and a homotriglyceride comprising three fatty acid moieties each with 10 carbon atoms can be synthesized by esterification of glycerol with C10 fatty acids (e.g., decanoic acid).

In an embodiment, the composition comprises MCTs comprising at least one octanoic acid moiety or decanoic acid moiety, and the composition is free from or substantially free from any other triglycerides. As used herein, the term "free from any other triglycerides" means that the composition does not comprise any triglycerides that do not contain at least one octanoic acid moiety or decanoic acid moiety. As used herein, the term "substantially free from any other triglycerides" means that the composition may contain traces of other triglycerides, i.e., less than 5 mol %, preferably less than 3 mol %, more preferably less than 2 mol %, even more preferably less than 1 mol % or most preferably less than 0.5 mol %.

After oral absorption, MCTs are metabolized to free fatty acids and further metabolized to ketones. The free fatty acids are initially metabolized to β-hydroxybutyrate (BHB) and then aceto acetate (AcA). MCFA and ketones can be produced in various amounts in bodily fluids depending on the MCT utilized, and they may be used as an alternative source of energy to glucose or to supplement the energy derived from glucose.

Ketones can be transported to the brain by, for example, monocarboxylic transporter 1 (MCT1) where they are mainly metabolized by neurons. Free fatty acids, such as C8 free fatty acids and C10 free fatty acids, can reach the brain by diffusion where they are mainly metabolized by astrocytes.

Oral administration of the composition to the subject provides one or more of ketones, C8 fatty acids, or C10 fatty acids to a bodily fluid of that subject. The exposure of the subject to ketones and/or specific fatty acids (e.g., C8 or C10 fatty acids) can be quantified by measuring the levels of ketones and/or specific fatty acids in the subject's plasma, e.g., over 8 hours following oral administration. The exposure of a subject to a ketone and/or specific fatty acids may be calculated by determining the area under the curve (AUC) in a plot of concentration of ketone and/or fatty acid in a bodily fluid e.g., blood plasma, against time (e.g., over 8 or 24 hours). Biological fluids can be treated prior to analysis with organic solvent to precipitate protein and reconstituted in a mass spectrometry (MS) compatible solvent. Levels of ketone bodies and medium chain fatty acids can be assessed using liquid chromatography coupled to high resolution mass spectrometry (LC-MS). In particular, β-hydroxybutyrate (BHB), aceto acetate (AcA), and specific fatty acid concentrations can be quantitatively measured using an external calibration methodology.

In an embodiment, the protein is selected from the group consisting of dairy based proteins, plant based proteins, animal based proteins, artificial proteins, or combinations thereof.

Dairy based proteins include, for example, casein, casein hydrolysates, caseinates (e.g., all forms including sodium, calcium, potassium caseinates), whey hydrolysates, whey (e.g., all forms including concentrate, isolate, demineralized), milk protein concentrate, and milk protein isolate. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, and any proteins derived from beans, buckwheat, lentils, and pulses. Animal based proteins may include, for example, beef, poultry, fish, lamb, seafood, pork, egg, or combinations thereof.

In an embodiment the protein source is a dairy based protein. In an embodiment the dairy based proteins are selected from the group consisting of casein, caseinates, casein hydrolysates, whey, whey hydrolysates, milk protein concentrate, milk protein isolate, or combinations thereof.

The composition may further comprise one or more additional components such as minerals; vitamins; salts; or functional additives including, for example, palatants, colorants, emulsifiers, antimicrobial or other preservatives. Non-limiting examples of suitable minerals for the compositions disclosed herein include calcium, phosphorous, potassium, sodium, iron, chloride, boron, copper, zinc, magnesium, manganese, iodine, selenium, chromium, molybdenum, fluoride and any combination thereof. Non-limiting examples of suitable vitamins for the compositions disclosed herein include water-soluble vitamins (such as thiamin (vitamin B1), riboflavin (vitamin B2), niacin (vitamin B3), pantothenic acid (vitamin B5), pyridoxine (vitamin B6), biotin (vitamin B7), myo-inositol (vitamin B8), folic acid (vitamin B9), cobalamin (vitamin B12), and vitamin C) and fat-soluble vitamins (such as vitamin A, vitamin D, vitamin E, and vitamin K) including salts, esters or derivatives thereof. Inulin, taurine, carnitine, amino acids, enzymes, coenzymes, and any combination thereof may be included in various embodiments.

In one embodiment, the composition further comprises at least one of pyridoxine (vitamin B6), folic acid (vitamin B9), or cobalamin (vitamin B12). Folate (vitamin B9) supplementation is beneficial for memory, better cognitive function, and psychomotor speed. Vitamin B12 deficiency is primarily related to altered absorption in the elderly. Vitamin B12 and folic acid deficiencies result in symptoms such as low mood, fatigue, irritability. Further, folate and vitamin B12 are required for the synthesis of neurotransmitters.

The composition may further comprise one or more agents that promote or sustain general neurologic health or further enhance cognitive function. Examples of such agents include choline, phosphatidylserine, alpha-lipoic acid, CoQ10, acetyl-L-carnitine, omega-3 fatty acid, herbal extracts (such as *Gingko biloba, Bacopa monniera, Convolvulus pluricaulis* and *Leucojum aestivum*).

The composition may be in the form of a medical food. The term "medical food" as used herein refers to a food product specifically formulated for the dietary management of a medical disease or condition; for example, the medical disease or condition may have distinctive nutritional needs that cannot be met by normal diet alone. The medical food may be administered under medical supervision. The medical food may administered orally or as a tube feed. The term "tube feed" refers to a product which is intended for introducing nutrients directly into the gastrointestinal tract of a subject by a feeding tube. A tube feed may be administered by, for example, a feeding tube placed through the nose of a subject (such as nasogastric, nasoduodenal, and nasojejunal tubes) or a feeding tube placed directly into the abdomen of a subject (such as gastrostomy, gastrojejunostomy, or jejunostomy feeding tube).

The composition may be in the form of a nutritional composition or a nutritional supplement. The term "nutritional supplement" refers to a product which is intended to supplement the general diet of a subject.

The composition may be in the form of a complete nutritional product. The term "complete nutritional product" refers to a product which is capable of being the sole source of nutrition for the subject.

In various embodiments, the composition may be in the form of a beverage, mayonnaise, salad dressing, margarine, low fat spread, dairy product, cheese spread, processed cheese, dairy dessert, flavoured milk, cream, fermented milk product, cheese, butter, condensed milk product, ice cream mix, soya product, pasteurised liquid egg, bakery product, confectionary product, confectionary bar, chocolate bar, high fat bar, liquid emulsion, spray-dried powder, freeze-dried powder, UHT pudding, pasteurised pudding, gel, jelly, yoghurt, or a food with a fat-based or water-containing filling.

In an embodiment, the composition may be an infant formula. In yet other embodiments, the composition may be used to coat a food, snack, pet food, or pet treat.

The compositions disclosed herein may be administered enterally or parenterally. Preferably, the composition is administered enterally. For example, the composition may be administered in the form of a food stuff or a supplement. Enteral administration may be oral, gastric, and/or rectal. Preferably the composition is administered orally.

The subject may be a mammal such as a human, canine, feline, equine, caprine, bovine, ovine, porcine, cervine or a primate. Preferably the subject is a human. In an embodiment, the subject is an infant. The infant may, for example, be a human such as a newborn infant (i.e., a baby under 28 days of age) or a premature infant (i.e., a baby born before 37 completed weeks of gestation).

In an embodiment, the subject is an aging subject. For instance, a subject may be an aging subject when it has reached 40, 50, 60, 66, 70, 75, or 80% of its likely lifespan. A determination of lifespan may be based on actuarial tables, calculations, or estimates, and may consider past, present, and future influences or factors that are known to positively or negatively affect lifespan. Consideration of species, gender, size, genetic factors, environmental factors and stressors, present and past health status, past and present nutritional status, and stressors may be taken into consideration when determining lifespan. The aging subject may, for example, be a human subject over the age of 40, 45, 50, 55, 60, 65, 70, 75, 80, 85, 90, 95 or 100 years old.

In an embodiment, the subject is a subject diagnosed with mild cognitive impairment or suffering from memory complains. The subject may need improving cognition such as particularly episodic memory, executive function, and language. The subject may have or suffer from a brain energy deficiency condition or disease, neurological condition, and/or cognitive impairment.

All references herein to treatment include curative, palliative and prophylactic treatment. Treatment may also include arresting progression in the severity of a disease. Both human and veterinary treatments are within the scope of the present disclosure.

Free fatty acids and ketones produced from MCTs can provide an alternative energy source to glucose to supplement or replace the energy in cells such as astrocytes, myocytes, cardiomyocytes, or neuronal cells.

Brain tissue consumes a large amount of energy in proportion to its volume. In an average healthy subject, the brain obtains most of its energy from oxygen-dependent metabolism of glucose. Typically, the majority of the brain's energy is used to help neurons or nerve cells send signals and the remaining energy is used for cell-health maintenance. A deficiency in brain energy, for example caused by impairment of glucose utilisation, can result in neuronal hyperactivity, seizures and cognitive impairments.

Examples of brain energy deficiency conditions or diseases include: migraine, memory disorder, age-related memory disorder, brain injury, neurorehabilitation, stroke and post-stroke, amyloid lateral sclerosis, multiple sclerosis, cognitive impairment, mild cognitive impairment (MCI), cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy.

As used herein, the term "neurological condition" refers to a disorder of the nervous system. Neurological conditions may result from damage to the brain, spinal column or nerves, caused by illness or injury. Non-limiting examples of the symptoms of a neurological condition include paralysis, muscle weakness, poor coordination, loss of sensation, seizures, confusion, pain and altered levels of consciousness. An assessment of the response to touch, pressure, vibration, limb position, heat, cold, and pain as well as reflexes can be performed to determine whether the nervous system is impaired in a subject.

Some neurological conditions are life-long, and the onset can be experienced at any time. Other neurological conditions, such as cerebral palsy, are present from birth. Some neurological conditions, such as Duchenne muscular dystrophy, commonly appear in early childhood, while other neurological conditions, such as Alzheimer's disease and Parkinson's disease, affect mainly older people. Some neurological conditions have a sudden onset due to injury or illness, such as a head injury or stroke, or cancers of the brain and spine.

In an embodiment, the neurological condition is the result of traumatic damage to the brain. Additionally or alternatively, the neurological condition is the result of an energy deficiency in the brain or in the muscles.

Examples of neurological conditions include migraine, memory disorder, age-related memory disorder, brain injury, neurorehabilitation, stroke and post-stroke, amyloid lateral sclerosis, multiple sclerosis, cognitive impairment, mild cognitive impairment (MCI), cognitive impairment post-intensive care, age-induced cognition impairment, Alzheimer's disease, Parkinson's disease, Huntingdon's disease, inherited metabolic disorders (such as glucose transporter type 1 deficiency syndrome and pyruvate dehydrogenase complex deficiency), bipolar disorder, schizophrenia, and/or epilepsy.

A migraine is an intense headache accompanied by other symptoms such as nausea (feeling sick), visual problems and an increased sensitivity to light or sound. A migraine may be preceded by an aura; the main symptoms of an aura are visual problems such as blurred vision (difficulty focusing), blind spots, flashes of light, or a zigzag pattern moving from the central field of vision towards the edge.

Strokes (also known as cerebrovascular accident (CVA) and cerebrovascular insult (CVI)) occur when there is poor blood flow to the brain resulting in cell death. There are two main types of stroke: ischemic (due to lack of blood flow) and haemorrhagic (due to bleeding). Strokes result in part of the brain not functioning properly. The signs and symptoms of a stroke may include an inability to move or feel on one side of the body, problems understanding or speaking, feeling like the world is spinning, or loss of vision to one side. The signs and symptoms often appear soon after the stroke has occurred.

Amyotrophic lateral sclerosis (ALS) (also known as Lou Gehrig's disease, Charcot disease and motor neuron disease), involves the death of neurons responsible for controlling voluntary muscles. ALS is characterized by stiff muscles, muscle twitching, and gradually worsening weakness due to muscle wasting; this results in difficulty speaking, swallowing, and eventually breathing.

Multiple sclerosis affects the nerves in the brain and spinal cord, causing a wide range of symptoms including problems with muscle movement, problems with mobility and balance, numbness and tingling, blurring of vision (typically there is loss of vision in one eye) and fatigue.

Parkinson's disease is a degenerative disorder of the central nervous system mainly affecting the motor system. In the early course of the disease, the most obvious symptoms are movement-related; these include tremor at rest, rigidity, slowness of movement and difficulty with walking and gait. Later in the course of the disease, thinking and behavioral problems may arise, with dementia commonly occurring in the advanced stages of the disease. Other symptoms include depression, sensory, sleep and emotional problems.

Alzheimer's disease is a progressive neurodegenerative disorder. Alzheimer's disease is the most common cause of dementia. Symptoms include memory loss and difficulties with thinking, problem-solving or language. The mini mental state examination (MMSE) is an example of one of the tests used to diagnose Alzheimer's disease.

Huntington's disease is an inherited condition that damages certain nerve cells in the brain. Huntington's disease affects muscle coordination and leads to mental decline and behavioral symptoms. The earliest symptoms are often subtle problems with mood or cognition. A general lack of coordination and an unsteady gait often follow. As the disease advances, uncoordinated, jerky body movements become more apparent, along with a decline in mental abilities and behavioral symptoms. Physical abilities gradually worsen until coordinated movement becomes difficult. Mental abilities generally decline into dementia.

Inherited metabolic disorders are a range of diseases caused by defective genes. Typically the defective gene(s) results in a defect in an enzyme or in a transport protein which results in a block in the way that a compound is processed by the body such that there is a toxic accumulation of the compound. Inherited metabolic disorders can affect any organ and usually affect more than one. Symptoms often tend to be nonspecific and usually relate to major organ dysfunction or failure. The onset and severity of a metabolic disorder may be exacerbated by environmental factors, such as diet and concurrent illness.

Glucose transporter type 1 (Glut1) deficiency syndrome is a genetic metabolic disorder involving the GLUT1 protein which transports glucose across the blood-brain barrier or the boundary separating tiny blood vessels from brain tissue. The most common symptom is seizures (epilepsy), which usually begin within the first few months of life. Additional symptoms that can occur include varying degrees of cognitive impairment and movement disorders characterized by ataxia, dystonia, and chorea. Glut1 deficiency syndrome may be caused by mutations in the SLC2A1 gene which produce GLUT1 protein.

Pyruvate dehydrogenase complex deficiency (pyruvate dehydrogenase deficiency or PDCD) is a neurodegenerative disorder associated with abnormal mitochondrial metabolism and disrupted carbohydrate metabolism. PDCD is characterized by the buildup of lactic acid in the body and a variety of neurological problems. Signs and symptoms of this condition usually first appear shortly after birth, and they can vary widely among affected individuals. The most common feature is a potentially life-threatening buildup of lactic acid (lactic acidosis), which can cause nausea, vomiting, severe breathing problems, and an abnormal heartbeat. Other symptoms include: neurological problems; delayed development of mental abilities and motor skills such as sitting and walking; intellectual disability; seizures; weak muscle tone (hypotonia); poor coordination, and difficulty walking. Some affected individuals have abnormal brain structures, such as underdevelopment of the tissue connecting the left and right halves of the brain (corpus callosum), wasting away (atrophy) of the exterior part of the brain known as the cerebral cortex, or patches of damaged tissue (lesions) on some parts of the brain.

PDCD is a deficiency of one of the proteins in the pyruvate dehydrogenase complex (PDC). The pyruvate dehydrogenase complex comprises three enzymes identified as E1, E2 and E3; the E1 enzyme contains subunits identified as alpha and beta. The most common form of PDCD is caused by an abnormal gene in the E1 alpha subunit (the PDHA1 gene) located on the X chromosome. Some PDCD cases are caused by a mutation in a gene in another subunit of the pyruvate dehydrogenase complex such as the PDHX gene, the PDHB gene, the DLAT gene, the PDP1 gene, and the DLD gene.

Bipolar disorder is a brain disorder that causes unusual shifts in mood, energy, activity levels, and the ability to carry out day-to-day tasks. Bipolar disorder is characterized by periods of elevated mood and periods of depression. Bipolar disorder can be diagnosed using the guidelines from the Diagnostic and Statistical Manual of Mental Disorders (DSM) or the World Health Organization's International Statistical Classification of Diseases and Related Health Problems.

Schizophrenia is a chronic, severe, and disabling brain disorder in which individuals interpret reality abnormally. Schizophrenia may result in some combination of hallucinations, hearing voices, delusions, and extremely disordered thinking and behavior. Schizophrenia can be diagnosed using the guidelines from the Diagnostic and Statistical Manual of Mental Disorders (DSM) or the World Health Organization's International Statistical Classification of Diseases and Related Health Problems.

Epilepsy is a neurological disorder in which nerve cell activity in the brain becomes disrupted, causing seizures or periods of unusual behavior, sensations and sometimes loss of consciousness.

The terms "cognitive impairment" and "cognition impairment" refer to disorders that give rise to impaired cognition, in particular disorders that primarily affect learning, memory, perception, and/or problem solving.

Cognitive impairment may occur in a subject after intensive care. Cognitive impairment may occur as part of the ageing process, e.g. mild cognitive impairment (MCI).

The term "cognition" refers to the set of all mental abilities and processes, including knowledge, attention, memory and working memory, judgment and evaluation, reasoning and "computation", problem solving and decision making, comprehension and production of language. Levels of and improvements in cognition can be readily assessed by the skilled person using any suitable neurological and cognitive tests that are known in the art, including cognitive tests designed to assess speed of information processing, executive function and memory. Suitable example tests include Mini Mental State Examination (MMSE), Cambridge Neuropsychological Test Automated Battery (CANTAB), Alzheimer's Disease Assessment Scale-cognitive test (ADAScog), Wisconsin Card Sorting Test, Verbal and Figural Fluency Test and Trail Making Test, Wechsler Memory scale (WMS), immediate and delayed Visual Reproduction Test (Trahan et al. Neuropsychology, 1988 19(3) p. 173-89), the Rey Auditory Verbal Learning Test (RAVLT) (Ivnik, R J. et al. Psychological Assessment: A Journal of Consulting and Clinical Psychology, 1990 (2): p. 304-312), electroencephalography (EEG), magnetoencephalography (MEG), Positron Emission Tomography (PET), Single Photon Emission Computed Tomography (SPECT), Magnetic Resonance Imaging (MRI), functional Magnetic Resonance Imaging (fMRI), computerized tomography and long-term potentiation.

EEG, a measure of electrical activity of the brain, is accomplished by placing electrodes on the scalp at various landmarks and recording greatly amplified brain signals. MEG is similar to EEG in that it measures the magnetic fields that are linked to electrical fields. MEG is used to measure spontaneous brain activity, including synchronous waves in the nervous system.

PET provides a measure of oxygen utilisation and/or glucose metabolism. In this technique, a radioactive positron-emitting tracer is administered, and tracer uptake by the brain is correlated with brain activity. These tracers emit gamma rays which are detected by sensors surrounding the head, resulting in a 3D map of brain activation. As soon as the tracer is taken up by the brain, the detected radioactivity occurs as a function of regional cerebral blood flow. During activation, an increase in cerebral blood flow and neuronal glucose metabolism can be detected within seconds.

Suitable analysis can also be based on neuropsychiatric testing, clinical examinations and individual complaints of loss of cognitive function (e.g. subjective memory loss). Further suitable tests may be based on assessments of locomotion, memory and attention, seizure susceptibility, and social interaction and/or recognition.

Memory disorders are the result of neurological damage to the brain structures such that the storage, retention and recollection of memories are hindered. Memory disorders can be progressive with age (e.g. Alzheimer's disease), or they can be immediately resulting, for example, from a head injury. Levels of and improvements in memory disorders can be readily assessed by the skilled person using any suitable tests that are known in the art such as Alzheimer's Disease Assessment Scale-cognitive test (ADAScog), Mini Mental State Examination (MMSE), computerized tomography (CT) scan, Magnetic Resonance Imaging (MRI), Single Photon Emission Computed Tomography (SPECT), Positron Emission Tomography (PET), and electroencephalography (EEG).

EXAMPLE

The following non-limiting example presents scientific data developing and supporting the concept of a composition to improve cognitive functioning, support memory and/or recall, provide energy and/or ketones to the brain, and/or prevent and/or treat mild cognitive impairment (MCI), made by pre-mixing MCT with protein/food matrix in a liquid format, as provided by the present disclosure.

Participants

Participants included male or female aged ☐ 55 years plus mild cognitive impairment based on the Peterson criteria (i) presence of a subjective memory complaint, (ii) objective evidence of cognitive impairment as assessed by a neuro-cognitive battery, (iii) absence of major depression (General Depression Scale score [GDS<10/30], and (iv) full autonomy of daily living based on a score of <15/24 on the instrumental activities of daily living score (French version of the Functional autonomy measurement system [SMAF-E]). Exclusion criteria included diagnosis of a major cog-nitive disorder according to the 5th Edition of the Diagnostic and Statistical Manual of Mental Disorders, use of an cholinesterase inhibitor, major depression, history of alcohol or substance abuse, cancer within the past 2 years, smoking, uncontrolled diabetes (fasting plasma glucose>7 mM or glycated hemoglobin>6.5%), overt evidence of heart, liver or renal disease, vitamin B12 deficiency, uncontrolled hypertension, dyslipidemia or thyroid disease.

Eligible participants first underwent a general cognitive evaluation using the Montreal Cognitive Assessment (MoCA; score of >18 to <26/30) and/or Mini-mental state exam (MMSE; score of >24 to <27/30), If eligible, this was followed by a detailed neurocognitive battery to determine whether there was a deficit in one or more cognitive domains compared to appropriate normative data (>1.5 SD below the mean) and to classify the participant as having amnestic MCI (at least one score>1.5 SD below the mean on the tests of episodic memory) or non-amnestic MCI (at least one score>1.5 SD below the mean on other cognitive domains excluding episodic memory). Screening tests for all partici-pants were reviewed by a collaborating physician and neu-ropsychologist prior to enrollment.

Eligible participants were assigned to the Active or Pla-cebo treatment using a randomization sequence with 1:1 allocation. 70 participants were randomised in seven con-secutive blocks of ten participants. Before starting the inter-vention, well-being and memory complaint questionnaires were completed by the participants and a fasting blood sample was drawn for metabolic and clinical chemistry measurements.

Participants received their supply of Active or Placebo drink at monthly visits and were encouraged to complete a daily logbook to monitor compliance. Telephone follow-up was done during the first month as needed. At each monthly visit, participants consumed their usual breakfast along with their experimental drink at home followed by a visit to the lab 1-2 h later during which a blood sample was drawn. They were asked to bring back unused bottles which were used to estimate compliance. They also met the research nurse to discuss concerns and any adverse events that might have occurred. The final 6-month visit was done 165±9 days after starting the intervention; a blood sample was obtained 1-2 h after taking breakfast and the final dose of the assigned supplement in the metabolic kitchen. Neurocognitive ques-tionnaires were completed during the final week of the intervention.

Participants were blinded to the drink's composition and instructed to take 125 ml of their assigned drink twice a day, usually with breakfast and again with supper (total of 250 ml/day). The daily dose was gradually increased from 50 ml to 125 ml/meal during the first 2 weeks.

Cognitive Tests

For eligibility, general cognitive status was assessed using the MMSE and the MoCA questionnaires. Eligible partici-pants subsequently completed a 90-minute neurocognitive test battery evaluating the five main domains of cognitive function, i.e. episodic memory, executive function, process-ing speed, attention, and language. Episodic memory was assessed by the French version of the 16-item free and cued word learning and recall test (Rappel Libre/Rappel Indicé

[RL/RI-16]) and the Brief Visual Memory Test-Revised (BVMT-R). The Trail Making, the Stroop Color and Word Interference test (Stroop), and the Verbal Fluency (VF) tests from the Delis-Kaplan Executive Function System provided information on executive function, attention and processing speed, respectively. The Digit Symbol Substitution Tests and the forward and backward digit span from the Wechsler Adult Intelligence Scale provided information on and pro-cessing speed and working memory, respectively. The Bos-ton Naming Test was for language ability. To minimize a potential learning effect on the post-supplementation test, two versions of validated word lists and stimulus pages were used in the RL/RI-16 and BVMT-R tests. These tests are commonly used in clinical settings and were administered by a trained rater using standardized testing procedures. Tables of normative scores from similar population was used to determine a Z-score for each sub-test.

Metabolic Study

Participants of the second phase of the trial were invited to undertake two identical metabolic study days, the first before starting the supplement and the second at the end of the 6-month supplementation period. The objective was to evaluate whether chronic ingestion of a kMCT changed the plasma ketone response. Briefly, after a 12 h overnight fast, participants received a standardized breakfast (two pieces of toast with raspberry jam, a piece of cheese, and two scrambled eggs; total of 470 calories, 19.5 g of fat, 24.2 g of protein and 55 g of carbohydrate) and a dose (125 ml) of the drink to which they had been randomized. Four hours later, a second dose of the same test drink was given but without food. Venous forearm blood samples were taken in EDTA tubes at baseline and every 30 min during the 8 h study period.

Results

The adjusted raw scores of the first free recall trial of the RL/RI-16 test improved in the Active group (multi-covari-ates model; p=0.042; FIGS. 1 and 4), a difference that remained significant after normalization for age, sex and education (Z-score change of −0.1 for Placebo vs +0.51 for active group, p=0.042; FIG. 2). No significant changes were observed in either group on the Brief Visual Memory Test-Revised (BVMT-R). Verbal fluency (categories) scores were significantly higher post-intervention in the Active group in (+1.9 words) compared to Placebo (−1.0 words; p=<0.005; FIGS. 1 and 5). Two measures of executive function showed improvement post-intervention in the Active group with significantly fewer errors on all condi-tions of the Trail making (p=0.020) and Stroop tests (p=0.042). The Boston naming test also showed improve-ment post-intervention in the Active group (+1.1 total cor-rect responses), while the Placebo group had 0.2 fewer total correct responses; p=0.018; FIG. 6). Attention and process-ing speed scores did not change significantly post-treatment in either group (data not shown). Post-intervention differ-ences in several cognitive tests had an effect size (partial re) between moderate (0.06) and large (0.14), including the raw and Z-scores of verbal fluency (categories), raw scores on the Trail making test (total errors), Z-scores on the Stroop test (errors, Inhibition-switching) and raw scores on the Boston naming test (FIGS. 1-2).

In ApoE4 (−), amnesic MCI and protocol-compliant par-ticipants, results for post-treatment differences in the Active group remained statistically different from Placebo on the Verbal Fluency (categories) test, and for total correct responses on the Boston naming test. Improvement on some sub-tests of the first free recall trial of the RL/RI-16 test was seen in these three sub-groups (FIGS. 9-11). ApoE4 (+)

participants on the Active treatment had better scores on immediate recall of the RL/RI-16 (0.8 more words recalled while those on Placebo had 0.9 fewer words recalled; p=0.036), on the Verbal Fluency (categories) test (p=0.048), and fewer total errors on the Trail making test (p=0.017; FIG. 12).

Figure 7:
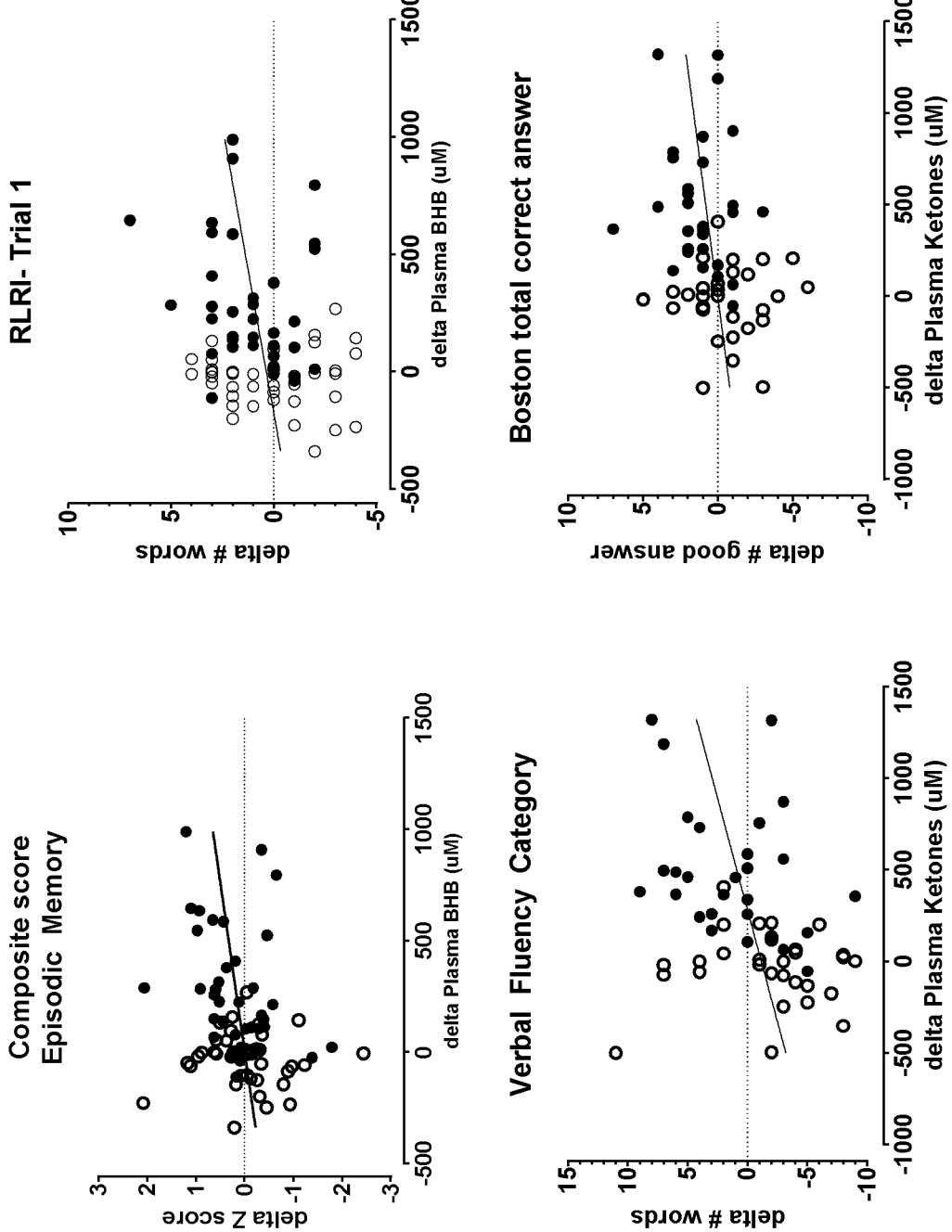
FIG. 7 are graphs showing the correlations between the change in plasma beta-hydroxybutyrate (BHB) or change in plasma total ketones (BHB+acetoacetate) for the composite Z-score for episodic memory (r=+0.229, p=0.042), Trial 1 of the RL/RI-16 test (r=+0.232, p=0.039), Verbal Fluency (categories) test (r=+0.325, p=0.013) and Boston naming test (total correct answers; r=+0.229, p=0.042).

The change in plasma ketones (BHB or total ketones) was significantly positively correlated to the change in several cognitive tests of episodic memory, executive function and language, with coefficients of +0.229 to 0.325 and p values from 0.042 to 0.0028 (FIG. 7). These correlation analyses were limited to cognitive tests in which differences between groups were observed on the raw or Z-scores (FIGS. 1-2). There was no change in the composite score of the different neurocognitive domains (FIG. 13) but the composite Z score for episodic memory correlated positively with BHB concentration (r=+0.229, p=0.042; FIG. 7).

Metabolic and Laboratory Results

Figure 8:
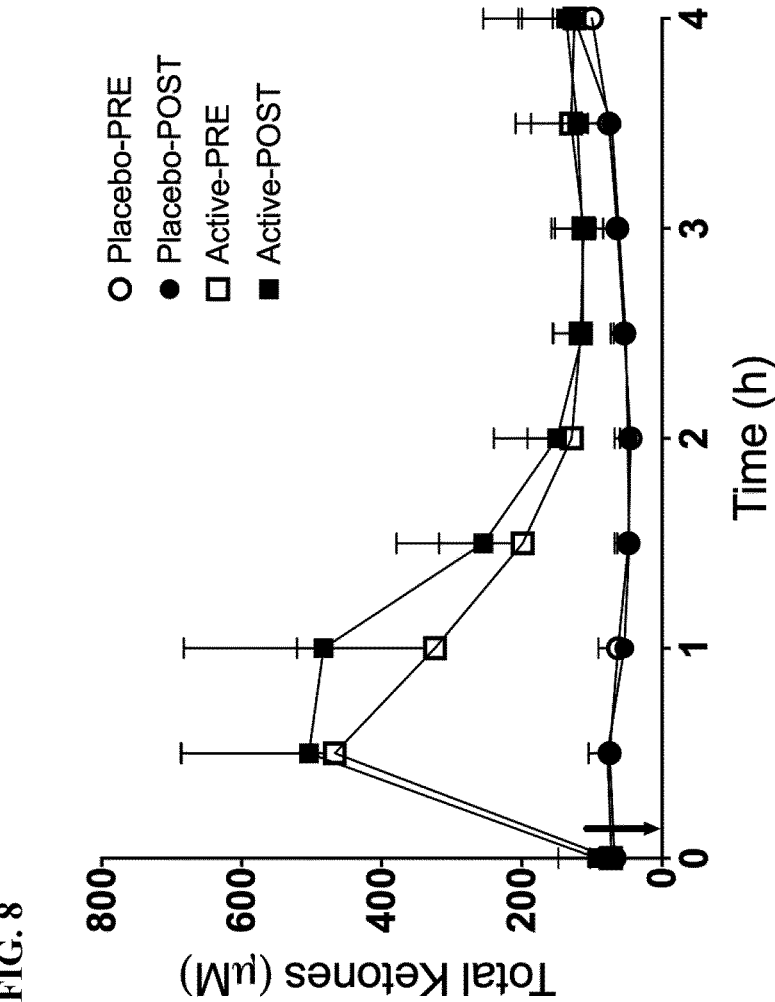
FIG. 8 is a graph showing the plasma total ketones throughout the 4 hour metabolic study day during which 2×15 g of MCT were consumed (arrows) before and after 6 months on 2×15 g/day of MCT. Data are means±SD.

After the 6-month supplementation, total plasma ketones, BHB and AcA all increased significantly in the Active group (p<0.0001; FIG. 3). There was no change in body mass index or body weight in either group. Following the intervention, glucose, cholesterol and aspartate transaminase were significantly higher in the Active group but remained within our institutional clinical reference range. No other changes in blood chemistry were observed (FIG. 3). There was no change in the plasma ketone response to 2×15 g of the kMCT or Placebo post- vs pre-intervention (FIG. 8).

The results showed that performance on widely used tests of episodic memory, executive function and language improved over six months in MCI when consuming 30 g/day of kMCT relative to a matching Placebo. Moderate to large effect sizes (partial n2 of 0.06 to 0.14) were observed in the Active group, suggesting that these cognitive improvements are clinically relevant, especially on tests of executive function and language (FIGS. 1-2). The positive correlation between change in plasma ketones and change in performance in several cognitive domains (FIG. 7) support the concept that ketones improve cognition in MCI by contributing to brain energy rescue.

The results demonstrated that with a liquid emulsion providing 30 g/day in two 15 g doses, kMCT has good ketone bioavailability and, when administered over six months, leads to improvements in cognition in MCI that are independent of age, sex, education, type of MCI and ApoE4 status (FIGS. 2-3 and 9-13).

The results also demonstrated the safety of chronic kMCT supplementation in an older population with MCI. Cardiometabolic outcomes were unchanged or remained within the normal reference range for age (FIG. 3), suggesting that concerns about saturated fat and weight gain or other aspects of cardiovascular health are not justified in this population in relation to consuming a kMCT (or the Placebo fat). The metabolic evaluation of the plasma ketone response in a subgroup (n=12 Placebo and n=10 Active) in the second phase of the trial showed that the increase in ketones was maintained throughout the 6-month test period, suggesting no significant change in ketone production or metabolism during this time frame (FIG. 8). Furthermore, older people have at least as good a ketone response to a 15 g dose of kMCT as younger adults, with a transient peak never exceeding 1.6 mM (BHB and AcA combined), which is a ketone level at least an order of magnitude below that associated with ketoacidosis.

Figure 14:
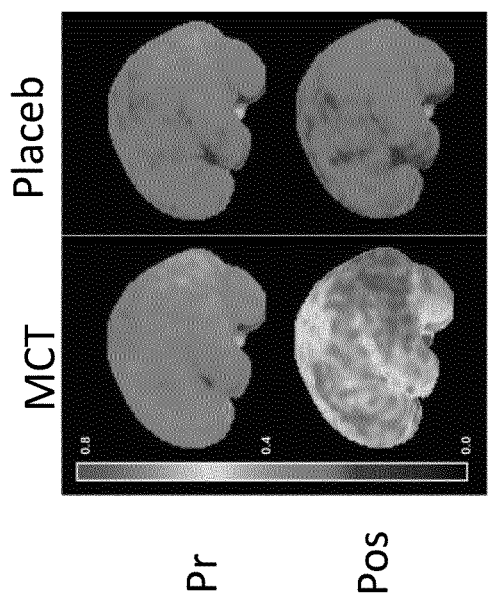
FIG. 14 show ketone PET images showing increased brain ketone uptake after the intervention according to the experimental example disclosed herein.
Figure 15:
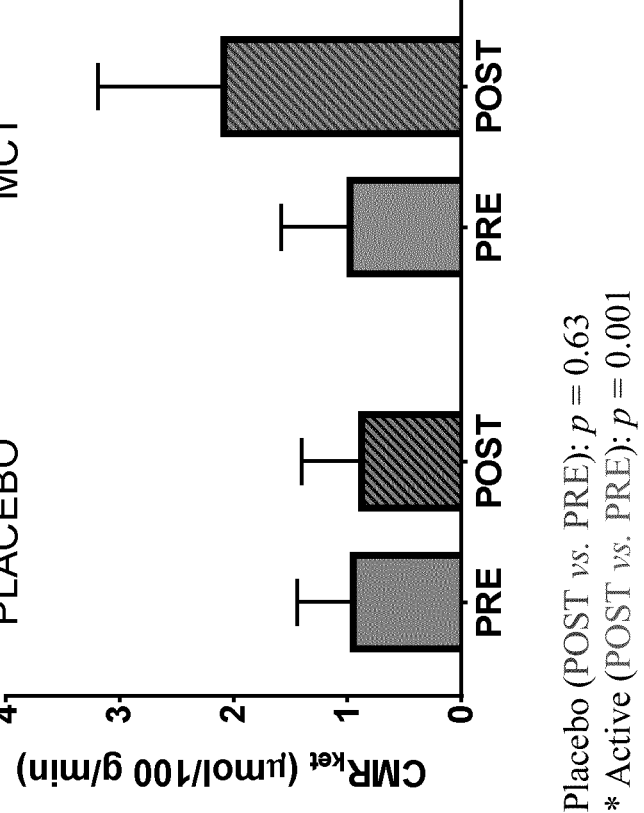
FIG. 15 is a graph showing the CMRket of PLACEBO and MCT before (PRE) and after (POST) the intervention according to the experimental example disclosed herein.

FIG. 14 show ketone PET images showing increased brain ketone uptake after the intervention according to the experimental example disclosed herein. FIG. 15 is a graph showing the CMRket of PLACEBO and MCT before (PRE) and after (POST) the intervention according to the experimental example disclosed herein. FIG. 16 is a table summarizing the cognitive tests according to the experimental example disclosed herein. FIG. 17 is a table summarizing the significant changes in the cognitive tests according to the experimental example disclosed herein. FIG. 18 is a table showing more details of the significant changes (FIG. 17) in the cognitive tests according to the experimental example disclosed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of improving cognitive functioning comprising at least one of episodic memory, executive function, or language skills of an individual, the method comprising administering to the individual a composition comprising medium chain triglycerides (MCTs) in a daily dosage from about 15 g to about 45 g MCTs, wherein the MCTs comprise octanoic acid and decanoic acid in a weight ratio of 60:40, wherein the composition is in the form of a solid powder, further comprises at least one of pyridoxine (vitamin B6), folic acid (vitamin B9), or cobalamin (vitamin B12), and wherein the daily dosage comprises at least two servings of the composition, each serving comprising about 15 g MCTs.

2. A method of supporting memory and/or recall in an individual, the method comprising administering to the individual a composition comprising medium chain triglycerides (MCTs) in a daily dosage from about 15 g to about 45 g MCTs, wherein the MCTs comprise octanoic acid and decanoic acid in a weight ratio of 60:40, wherein the composition is in the form of a solid powder, further comprises at least one of pyridoxine (vitamin B6), folic acid (vitamin B9), or cobalamin (vitamin B12), and wherein the daily dosage comprises at least two servings of the composition, each serving comprising about 15 g MCTs.

3. A method of preventing and/or treating mild cognitive impairment (MCI), the method comprising administering to the individual a composition comprising medium chain triglycerides (MCTs) in a daily dosage from about 15 g to about 45 g MCTs, wherein the MCTs comprise octanoic acid and decanoic acid in a weight ratio of 60:40, wherein the composition is in the form of a solid powder, further comprises at least one of pyridoxine (vitamin B6), folic acid (vitamin B9), or cobalamin (vitamin B12), and wherein the daily dosage comprises at least two servings of the composition, each serving comprising about 15 g MCTs.

4. The method of claim, 1 wherein the daily dosage comprises three servings of the composition, each serving comprising about 15 g MCTs.

5. The method of claim 1, wherein the composition is administered to the individual for at least about 6 months.

6. The method of claim 1, wherein the individual is 65 years or older.

7. The method of claim 1, wherein the individual has mild cognitive impairment (MCI).

8. The method of claim 1, wherein the individual suffers from at least one of memory deficit, impaired thinking skill comprising an inability to make sound decisions or exhibiting poor judgment, depression, or anxiety.

9. The method of claim 2, wherein the individual has or suffers from a brain energy deficiency condition or disease, neurological condition, and/or cognitive impairment.

10. The method of claim 1, wherein the individual has a condition selected from the group consisting of epilepsy, a neurological disease, a neurodegenerative disease, heart failure, inborn errors of metabolism, obesity, types 2 diabetes, nonalcoholic fatty liver disease (NAFLD), nonalcoholic steatohepatitis (NASH), cancer, a brain energy deficiency condition, a migraine, a memory disorder, an age-related memory disorder, a brain injury, a stroke, amyloid lateral sclerosis, multiple sclerosis, cognitive impairment, mild cognitive impairment (MCI), cognitive impairment post-intensive care, age-induced cognition impairment, Alzheimer's disease, Parkinson's disease, Huntingdon's disease, an inherited metabolic disorder, bipolar disorder, schizophrenia, and combinations thereof.

11. The method of claim 1, wherein the composition is in a form selected from the group consisting of a beverage, mayonnaise, salad dressing, margarine, low-fat spread, dairy product, cheese spread, processed cheese, dairy dessert, flavoured milk, cream, fermented milk product, cheese, butter, condensed milk product, ice cream mix, soya product, pasteurised liquid egg, bakery product, confectionary product, confectionary bar, chocolate bar, high fat bar, liquid emulsion, spray-dried powder, freeze-dried powder, UHT pudding, pasteurised pudding, gel, jelly, yoghurt, a food with a fat-based or water-containing filling, and combinations thereof.

12. The method of claim 1, wherein the composition further comprises at least one ingredient selected from the group consisting of (i) carbohydrates in a weight ratio of at least 0.1 g carbohydrate/1.0 g of the MCTs, (ii) lipids, other than the MCTs, in a weight ratio of at least 0.1 g lipids/1.0 g of the MCTs, and combinations thereof.

* * * * *